United States Patent [19]

Fauss et al.

[11] 4,238,407

[45] Dec. 9, 1980

[54] PROCESS FOR THE PREPARATION OF NITRO DIPHENYL AMINE DERIVATIVES

[75] Inventors: Rudolf Fauss, Cologne; Kuno Wagner, Leverkusen; Jan Mazanek, Cologne, all of Fed. Rep. of Germany

[73] Assignee: Bayer Aktiengesellschaft, Leverkusen, Fed. Rep. of Germany

[21] Appl. No.: 95,711

[22] Filed: Nov. 19, 1979

[30] Foreign Application Priority Data

Nov. 29, 1978 [DE] Fed. Rep. of Germany ....... 2851514

[51] Int. Cl.$^3$ ..................... C07C 87/60; C07C 121/78
[52] U.S. Cl. ........................... 260/465 E; 260/465 D; 560/22; 560/27; 560/29; 560/31; 560/32; 564/433

[58] Field of Search ................... 260/465 E, 571, 576; 560/32

[56] References Cited

U.S. PATENT DOCUMENTS 3,847,990 11/1974 Blahak ............................ 260/576

*Primary Examiner*—Dolph H. Torrence
*Attorney, Agent, or Firm*—Sprung, Felfe, Horn, Lynch & Kramer

[57] ABSTRACT

A process for the preparation of nitro-diphenyl amines is disclosed by decarboxylation of a urethane in the presence of a base at an elevated temperature using tetramethylene sulphone as reaction medium is disclosed. The urethane can be one formed by the reaction of a nitrophenol with an aromatic isocyanate.

12 Claims, No Drawings

PROCESS FOR THE PREPARATION OF NITRO DIPHENYL AMINE DERIVATIVES

The invention relates to a process for the preparation of nitro-diphenyl amine derivatives.

4-nitro-diphenyl amine can be obtained by reacting 4-nitro-chloro benzene with aniline (DE-OS (German Offenlegungsschrift No.) 10 30 834) or by reacting 4-nitro-chloro benzene with formanilide (DE-OS 1056 615). Furthermore it is known (U.S. Pat. No. 3,847,990) to obtain 4-nitro-diphenyl amine by reacting 4-nitrophenol with phenol isocyanate in the presence of alkaline catalysts and nitrobenzene as the solvent at temperatures in the region of 200° C. This process has a decisive disadvantage from the point of view of safety: alkali metal 4-nitro-phenolates can be formed from the 4-nitro-phenol used and from the alkali metal acetates, hydroxides and carbonates particularly suitable as alkaline catalysts, these alkali metal 4-nitrophenolates being precipitated in solid form from the nitrobenzene solution, particularly towards the end of the reaction. These alkali metal 4-nitro-phenolates are, as is known, liable to explode at high temperatures when in solid form.

A process has been found for the preparation of nitro-diphenyl amine derivatives by the reaction of a nitrophenol of the formula

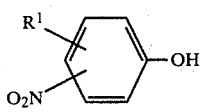

in which
R$^1$ represents hydrogen, alkyl, cycloalkyl, aryl, alkoxy, aryloxy, acyl, halogen, nitro or cyano,
with an aromatic isocyanate of the formula

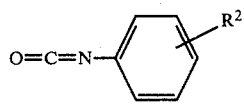

in which
R$^2$ represents hydrogen, alkyl, cycloalkyl, aryl, alkoxy, aryloxy, acyl, halogen, nitro or cyano
in the presence of a base within a temperature range of 100° to 250° C., the urethane forming intermediately being decarboxylated, characterised in that the process is conducted in tetramethylene sulphone as the reaction medium.

In the process according to the invention nitrophenols of formula (I) are preferably used, in which R$^1$ denotes hydrogen, alkyl, phenyl, alkoxy, phenyloxy or halogen.

Particularly preferred in the process according to the invention is the use of nitrophenols of formula (I), in which R$^1$ denotes hydrogen, methyl, methoxy, phenyloxy or chlorine.

Preferably an aromatic isocyanate of formula (II), in which R$^2$ denotes hydrogen, alkyl, phenyl, alkoxy, phenyloxy or halogen, is used in the process according to the invention.

The use of an aromatic isocyanate of formula (II), in which R$^2$ denotes hydrogen, methyl, methoxy, phenyloxy or chlorine, is particularly preferred in the process according to the invention.

Straight chained or branched hydrocarbon radicals with 1 to 6 carbon atoms may be mentioned as the alkyl, such as for example, methyl, ethyl, propyl, isopropyl, butyl, isobutyl, pentyl, isopentyl, hexyl or isohexyl. Preferred as the alkyl are hydrocarbon radicals with 1 to 4 carbon atoms, such as for example methyl, ethyl, propyl, isopropyl, butyl or isobutyl. The particularly preferred alkyl is the methyl radical.

Cyclic hydrocarbon radicals with 5 to 7 carbon atoms, which can optionally be substituted by low alkyl, may be mentioned as the cycloalkyl, such as for example cyclopentyl, methyl-cyclopentyl, cyclohexyl, methyl-cyclohexyl, cycloheptyl or methyl-cyclo-heptyl.

Aromatic hydrocarbon radicals with 6 to 14 carbon atoms, for example, phenyl naphthyl or anthryl, may be mentioned as the aryl. The preferred aryl is the phenyl radical.

As the alkoxy radicals may be mentioned which are derived from a low alcohol with 1 to 4 carbon atoms, for example, methoxy, ethoxy, propoxy, isopropoxy, butoxy or isobutyloxy. The preferred alkoxy is the methoxy radical.

As the aryloxy, radicals may be mentioned which are derived from an aromatic hydroxyl compound, such as for example phenoxy, naphthyloxy or anthryloxy. The preferred aryloxy is the phenoxy radical.

As the acyl, alkylcarbonyl radicals with 2 to 5 carbon atoms may be mentioned, such as for example acetyl, propionyl, butyryl or valeroyl. The preferred acyl is the acetyl radical.

Fluorine, chlorine or bromine, preferably chlorine may be mentioned as the halogen.

The following may be mentioned as examples of the nitrophenols to be used according to the invention: p-nitrophenol, o-nitrophenol, 2,4-dinitrophenol, 4-nitro-2-chlorophenol, 4-nitro-3-chlorphenol, 3-chloro-2-nitrophenol, 4-chloro-2-nitrophenol, 5-chloro-2-nitrophenol, 6-chloro-2-nitrophenol, 2,6-dichloro-4-nitrophenol, 4-nitroorthocresol, 4-nitro-metacresol, 6-nitroorthocresol, 6nitro-metacresol, 4-nitro-2-isoproplylphenol, 4-nitro-2-isobutylphenol, 4-nitro-2-cyclohexylphenol.

Examples which may be mentioned of aromatic isocyanates able to be used according to the invention are: phenyl isocyanate, m-methylphenyl isocyanate, p-methylphenyl isocyanate, m-isobutylphenyl isocyanate, m-2-ethylhexylphenyl isocyanate, m-cyclohexylphenyl isocyanate, m-chlorophenyl isocyanate, p-chlorophenyl isocyanate, m-nitrophenyl isocyanate, p-nitrophenyl isocyanate.

A urethane of the formula

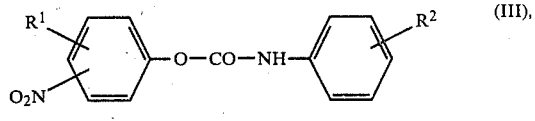

in which
R$^1$ and R$^2$ have the above mentioned meaning, can, of course, also be used instead of an optionally substituted nitrophenol and an optionally substituted aromatic isocyanate, which react in the reaction mixture accompanied by the formation of a urethane, the above urethane then being heated in the presence of a base to a temperature of approximately 100°–250° C. in tetramethylene sulphone as the reaction medium.

Urethanes of the formula (III) are able to be prepared according to known processes, for example by the reaction of optionally substituted nitrophenols with isocyanates (Ind. Eng. Chem., Anal. Ed. 16, 304 (1944)) or by the reaction of optionally substituted nitrophenyl-chlorocarbonic acid esters with optionally substituted amines (Liebigs Ann. Chem. 562, 205 (1949)).

The starting products in the process according to the invention can be used in the ratio of 0.5 to 5 mol of aromatic isocyanate to 1 mol of nitrophenol, preferably in the ratio of 1 to 2 mols of aromatic isocyanate to 1 mol of nitrophenol.

Basic inorganic or organic compounds may be mentioned as bases for the process according to the invention.

As basic inorganic compounds, basically reacting compounds of alkali metals and alkaline earth metals may be mentioned, for example their hydroxides, carbonates or basically reacting salts of organic acids, such as the acetates, formates, benzoates or phthalates.

As basic organic compounds, phenolates or substituted phenolates, such as nitrophenolates, of alkali metals, may be mentioned. In addition tertiary high-boiling amines and phosphines may be mentioned as basic organic compounds. Examples of the latter are N-methyl-bis($\beta$-hydroxyethyl-phenyl ether)-amine and tri-n-butyl-phosphine.

Preferred bases for the process according to the invention are the carbonates or hydroxides of sodium or potassium.

The base can be used in amounts of 0.5 to 50 mol %, preferably in amounts of 1 to 10 mol %, relative to the nitrophenol or nitrophenyl-N-phenyl urethane used.

As reaction temperature for the process according to the invention a range of 100° to 250° C., preferably a range of 150° to 220° C., may be mentioned.

The nitro-diphenyl amine derivatives which can be prepared in the process according to the invention can be represented by the formula

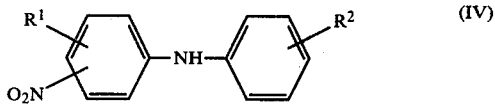

in which

R$^1$ and R$^2$ can be identical or different and denote hydrogen, alkyl, cycloalkyl, aryl, alkoxy, aryloxy, acyl, halogen, nitro or cyano.

Examples which may be mentioned of compounds of formula (IV) are: 2-nitro-diphenyl amine, 3-nitro-diphenyl amine, 4-nitro-diphenyl amine, 2-nitro-4-methyl-diphenyl amine, 4-nitro-2-methyl-diphenyl amine, 4-nitro-2-phenyl-diphenyl amine, 4-nitro-2-cyclohexyl-diphenyl amine, 4-nitro-2-methoxy-diphenyl amine, 2-nitro-4-acetyl-diphenyl amine, 2-nitro-4-acetyl-diphenyl amine, 2-nitro-4-chloro-diphenyl amine, 4-nitro-2-cyano-diphenyl amine, 2,4-dinitro-diphenyl amine, 2-nitro-4'-methyl-diphenyl amine, 4-nitro-4'-phenyl-diphenyl amine, 4-nitro-2'-methoxy-diphenyl amine, 2-nitro-4'-acetyl-diphenyle amine, 4-nitro-3'-methyl-diphenyl amine, 2,4'-dinitro-diphenyl amine, 2-nitro-2',4'-dimethyl-diphenyl amine, 4-nitro-2,4'-dichloro-diphenyl amine, 3-nitro-2,4'-dimethyl-diphenyl amine, 4-nitro-3'-chloro-diphenyl amine.

The process according to the invention can be conducted in the following way:

The optionally substituted nitrophenol is dissolved in tetramethylene sulphone (Sulfolan) and the basic compound is added. If the basic compound is added in the form of an aqueous solution, this water is subsequently removed by distillation. Then the mixture is heated to the desired temperature and the optionally substituted aromatic isocyanate is added dropwise whilst stirring vigorously.

Carbon dioxide evolution begins which can end after half and hour or up to 4 hours, depending on the amount of the starting mixture. Then the basic compound is neutralized by adding mineral acid. After filtering off any salts precipitated the majority of the Sulfolan is removed by distillation. The solid residue, which can still contain 1% to 5% by weight of Sulfolan, is purified further by means of conventional processing methods, for example by means of recrystallization from xylene. It is possible to free the mother liquor of the recrystallization step from solvent and to incorporate the residue obtained from this in a new starting mixture for the process according to the invention.

If, in the variant of the process, according to the invention, the starting compound is an optionally substituted nitrophenyl-N-phenyl urethane of formula (III), this can be dissolved in the Sulfolan and the alkaline compound is added. Then this reaction mixture is heated to the desired reaction temperature and the same procedure is followed as above.

The purified products thus obtained are of a purity of more than 96%. The process according to the invention has the following advantages:

1. No solid alkali metal 4-nitrophenolate is precipitated from the reaction mixture. Thus the process according to the invention is not dangerous, in contrast to the process of U.S. Pat. No. 3,847,990.

2. The triphenyl isocyanurate to be expected in small quantities as secondary product, which can be formed from the aromatic isocyanate, remains, as opposed to the nitrophenol process, in solution, so that incrustation of the reaction apparatus is avoided.

3. The yield of worked-up, pure nitrodiphenyl amine is approximately up to 10% higher in the process according to the invention than in the process of the named U.S. Pat. No.

4. The reaction speed is approx. 3 times' greater in the Sulfolan used according to the invention than in nitrobenzene, although the conditions are otherwise the same. At the same time higher concentrations of the reaction components can be used in the process when using Sulfolan than when using nitrobenzene. This produces a considerable increase in the space/time yield.

It is surprising that by the use, according to the invention, of tetramethylene sulphone as the reaction medium, a process was able to be achieved which is satisfactory as far as safety of operation is concerned and which, in addition, produces a higher yield than that of the prior art. This is all the more surprising because of the high boiling point of tetramethylene sulphone and its high polarity caused one to expect difficult separation from the reaction product.

Nitrodiphenyl amine and its derivatives are important intermediate products for the synthesis of p-alkylamino-diphenyl amine and p-dialkylamino-diphenyl amine, which, as stabilizers, almost completely prevent the oxidation (by oxygen) of natural and synthetic rubbers.

Thus, for example, p-nitrodiphenylamine is partly reduced by electrolysis in a nearly neutral reaction medium consisting of acetic acid, sodium acetate, ethanol and ethyl acetate to p-nitroso diphenylamine (Houben-Weyl, Methoden der Organischen Chemie [methods in organic chemistry], 4th ed., Vol. X/1, part 1, page 1064, Georg Thieme Verlag, Stuttgart (1971)) which itself is reacted with 2-octanone and hydrogen in one step at elevated temperatures (50° to 150° C.) in the presence of catalysts such as platinum, Raney nickel or copper oxide-chromium oxide combinations to yield N-phenyl-N'-2-octyl-p-phenylenediamine as a valuable stabilizer for natural and synthetic rubbers (U.S. Pat. No. 3,163,616).

EXAMPLE 1

150.2 g (1.08 mol) p-nitrophenol are dissolved in 750 ml Sulfolan and 5.52 g (0.04 mol) potassium carbonate in 10 ml water are added. The water is distilled off in vacuo and at 250° C. 129.7 g (1.09 mol) phenyl isocyanate are added dropwise over a period of 1 hour while stirring vigorously. After a further 1.5 hours approximately 24 l of $CO_2$ have evolved. At 150° C. the reaction mixture is reacted with 2.2 ml of concentrated $H_2SO_4$, stirred again briefly and filtered over a glass-sintering suction filter. The Sulfolan is almost completely distilled off in a film evaporator at 1 to 2 mm Hg.

234 g crude product remain, which are recrystallized from 620 ml xylene. 185 g (86.5% of the theoretical yield) 4-nitro-diphenyl amine are obtained. M.P.: 129° to 130° C.

EXAMPLE 2

The same method is followed as in Example 1, but using:
270.4 g (1.94 mol) p-nitrophenol,
750 ml Sulfolan, 9.94 g (0.072 mol) potassium carbonate, 214 g (189 mol) phenyl isocyanate,
4 ml concentrated sulphuric acid.
182.8 g = 85.4% of the theoretical yield of 4-nitro-diphenyl amine were obtained; m.p.: 130° to 131° C.

EXAMPLE 3

Same procedure as in Example 2, but with 8.1 g (0.14 mol) potassium hydroxide. 188.1 g = 87.9% of the theoretical yield of 4-nitro-diphenyl amine were able to be isolated: m.p.: 129° to 130° C.

EXAMPLE 4

The same method is followed as described in Example 1, except that the process is conducted using 167.4 g (1.09 mol) m-chlorophenyl isocyanate. 165.3 g (66.5% of the theoretical yeild) of 4-nitro-3'-chloro-diphenyl amine are obtained. M.p.: 127° to 128° C.

EXAMPLE 5

The same method is followed as described in Example 1, except that the process is conducted using 167.4 g (1.09 mol)p-chlorophenyl isocyanate. 159 g (64% of the theoretical yield) of 4-nitro-4'-chloro-diphenyl amine are obtained. M.p.: 179° to 180° C.

EXAMPLE 6

The same method is followed as described in Example 1, except that the process is conducted using 145.1 g (1.09 mol) m-methyl phenyl isocyanate. 182.6 g (80.1% of the theoretical yield) of 4-nitro-3'-methyl-diphenyl amine are obtained M.p.: 129° to 130° C.

What is claimed is:

1. A process for the production of a nitro-diphenyl amine which comprises decarboxylating a urethane of the formula

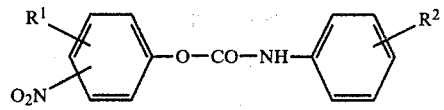

wherein
$R^1$ denotes hydrogen, alkyl, cycloalkyl, aryl, alkoxy, aryloxy, acyl, halogen, nitro or cyano and
$R^2$ denotes hydrogen, alkyl, cycloalkyl, aryl alkoxy, aryloxy, acyl, halogen, nitro or cyano by heating the same in the presence of a base at a temperature of 100° to 250°, characterized in that the process is conducted in tetramethylene sulphone as the reaction medium.

2. A process according to claim 1 wherein said urethane is formed by the reaction of a nitrophenol of the formula

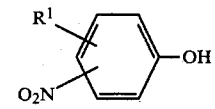

wherein $R^1$ has the above-described significance with an aromatic isocyanate of the formula

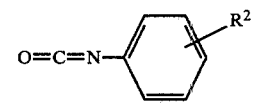

wherein $R^2$ has the above-described significance.

3. A process according to claim 2 wherein 0.5 to 5 mols of aromatic isocyanate are reacted per mol of nitrophenol.

4. A process according to claim 3 wherein 1 to 2 mols of aromatic isocyanate are reacted per mol of nitrophenol.

5. A process according to claim 1 wherein the urethane is heated at a temperature of 150° to 220° C.

6. A process according to claim 1 wherein the base is a basic inorganic or organic compound.

7. A process according to claim 1 wherein a basic inorganic compound is employed and said compound is an alkali metal or alkaline earth metal hydroxide or carbonate.

8. A process according to claim 1 wherein the base is a basically reacting salt of an organic acid.

9. A process according to claim 1 wherein the base is a phenolate or a substituted phenolate or a tertiary high boiling amine or phosphine.

10. A process according to claim 1 wherein said base is present at an amount of 0.5 to 50 mol percent based upon the weight of urethane.

11. In a process for the preparation of a nitro-diphenyl amine by reacting a nitrophenol of the formula

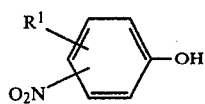

wherein

R¹ denotes hydrogen, alkyl, cycloalkyl, aralkyl, aralkoxy, aryloxy, acyl, halogen, nitro or cyano with an aromatic isocyanate of the formula

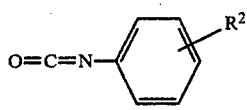

wherein

R² denotes hydrogen, alkyl, cycloalkyl, aryl, alkoxy, aryloxy, acyl, halogen, nitro or cyano in the presence of the base at a temperature in the range of 100° to 250° C. followed by decarboxylation of the urethane so formed the improvement wherein the reaction is carried out employing tetramethylene sulphone as the reaction medium.

12. A process according to claim 11 wherein the base is present in the amount of 0.5 to 50 mol percent based upon the amount of nitrophenol and the reaction is conducted at a temperature of 150° to 220° C.

* * * * *